(12) United States Patent
Bach et al.

(10) Patent No.: US 7,956,180 B2
(45) Date of Patent: Jun. 7, 2011

(54) DRIED AND AGGLOMERATED HYALURONIC ACID PRODUCT

(75) Inventors: Poul Bach, Birkerod (DK); Eric Thwaites, Copenhagen (DK)

(73) Assignee: Novozymes A/S, Bagsvaerd (DK)

( * ) Notice: Subject to any disclaimer, the term of this patent is extended or adjusted under 35 U.S.C. 154(b) by 21 days.

(21) Appl. No.: 11/132,829

(22) Filed: May 19, 2005

(65) Prior Publication Data

US 2005/0267068 A1 Dec. 1, 2005

Related U.S. Application Data

(60) Provisional application No. 60/577,846, filed on Jun. 7, 2004.

(30) Foreign Application Priority Data

| May 27, 2004 | (DK) | .................................. | 2004 00833 |
| Jun. 25, 2004 | (DK) | .................................. | 2004 01003 |
| Feb. 15, 2005 | (DK) | .................................. | 2005 00223 |

(51) Int. Cl.
*C07H 5/04* (2006.01)
*C07H 5/06* (2006.01)
*A01K 43/04* (2006.01)
*A61K 31/75* (2006.01)

(52) U.S. Cl. ........................................ 536/55.1; 514/54
(58) Field of Classification Search .................. None
See application file for complete search history.

(56) References Cited

U.S. PATENT DOCUMENTS

| 3,687,640 A | | 8/1972 | Sams et al. | |
| 3,700,461 A | * | 10/1972 | Dickens | .................. 426/285 |
| 4,754,027 A | | 6/1988 | Applegren | |
| 4,957,744 A | * | 9/1990 | della Valle et al. | ............ 424/401 |
| 5,095,037 A | | 3/1992 | Iwamitsu et al. | |
| 5,171,562 A | | 12/1992 | Bridges | |
| 5,356,883 A | * | 10/1994 | Kuo et al. | ..................... 514/54 |
| 5,616,568 A | * | 4/1997 | Pouyani et al. | .................. 514/54 |
| 5,718,922 A | * | 2/1998 | Herrero-Vanrell et al. | ... 424/501 |
| 6,495,148 B1 | * | 12/2002 | Abbiati | ..................... 424/401 |
| 6,537,978 B1 | * | 3/2003 | Turley et al. | .................... 514/54 |
| 6,806,259 B2 | * | 10/2004 | Udell et al. | ..................... 514/54 |
| 2002/0173484 A1 | * | 11/2002 | Leneau | ............................ 514/54 |

FOREIGN PATENT DOCUMENTS

| GB | 2218429 | 11/1989 |
| WO | WO 02/09787 | 2/2002 |
| WO | WO 0209787 | 2/2002 |
| WO | WO 03/080827 | 10/2003 |
| WO | WO03080827 | 10/2003 |

OTHER PUBLICATIONS

Definition of solubility from http://wordnet.princeton.edu.*
Miller-Liveney et al. 1997 J Dairy Sci. 80:447-456.*
Laurent et al., The FASEB Journal, vol. 6, pp. 2397-2404 (1992).
Toole et al., Cell Biology of the Extracellular Matrix, pp. 305-341 (1991).

* cited by examiner

*Primary Examiner* — Layla Bland
(74) *Attorney, Agent, or Firm* — Elias Lambiris (57) ABSTRACT

The present invention relates to products comprising hyaluronic acid or a salt thereof, which product is dried and agglomerated as defined herein, various compositions and articles comprising the product or compositions of the invention, methods of producing the product of the invention, and uses thereof.

26 Claims, 5 Drawing Sheets

Fig. 2 - Panel A

Fig. 2 - Panel B

Fig. 3 - Panel A

Fig. 3 - Panel B

Fig. 4 - Panel A

Fig. 4 - Panel B

Fig. 5 - Panel A

Fig. 5 - Panel B

DRIED AND AGGLOMERATED HYALURONIC ACID PRODUCT

CROSS-REFERENCE TO RELATED APPLICATIONS

This application claims priority or the benefit under 35 U.S.C. 119 of Danish application nos. PA 2004 00833, PA 2004 01003, and PA 2005 00223, filed May 27, 2004, Jun. 25, 2004, and Feb. 15, 2005, respectively, and U.S. provisional application No. 60/577,846 filed Jun. 7, 2004, the contents of which are fully incorporated herein by reference.

FIELD OF THE INVENTION

The present invention relates to a dried and agglomerated product comprising hyaluronic acid or a salt thereof, as well as to various compositions and articles comprising the product or compositions of the invention, methods of producing the product of the invention, and uses thereof.

BACKGROUND OF THE INVENTION

The most abundant heteropolysaccharides of the body are the glycosaminoglycans. Glycosaminoglycans are unbranched carbohydrate polymers, consisting of repeating disaccharide units (only keratan sulphate is branched in the core region of the carbohydrate). The disaccharide units generally comprise, as a first saccharide unit, one of two modified sugars —N-acetylgalactosamine (GalNAc) or N-acetylglucosamine (GlcNAc). The second unit is usually an uronic acid, such as glucuronic acid (GlcUA) or iduronate.

Glycosaminoglycans are negatively charged molecules, and have an extended conformation that imparts high viscosity when in solution. Glycosaminoglycans are located primarily on the surface of cells or in the extracellular matrix. Glycosaminoglycans also have low compressibility in solution and, as a result, are ideal as a physiological lubricating fluid, e.g., joints. The rigidity of glycosaminoglycans provides structural integrity to cells and provides passageways between cells, allowing for cell migration. The glycosaminoglycans of highest physiological importance are hyaluronan, chondroitin sulfate, heparin, heparan sulfate, dermatan sulfate, and keratan sulfate. Most glycosaminoglycans bind covalently to a proteoglycan core protein through specific oligosaccharide structures. Hyaluronan forms large aggregates with certain proteoglycans, but is an exception as free carbohydrate chains form non-covalent complexes with proteoglycans.

Numerous roles of hyaluronan in the body have been identified (see, Laurent T. C. and Fraser J. R. E., 1992, FASEB J. 6: 2397-2404; and Toole B. P., 1991, "Proteoglycans and hyaluronan in morphogenesis and differentiation." In: Cell Biology of the Extracellular Matrix, pp. 305-341, Hay E. D., ed., Plenum, New York). Hyaluronan is present in hyaline cartilage, synovial joint fluid, and skin tissue, both dermis and epidermis. Hyaluronan is also suspected of having a role in numerous physiological functions, such as adhesion, development, cell motility, cancer, angiogenesis, and wound healing. Due to the unique physical and biological properties of hyaluronan, it is employed in eye and joint surgery and is being evaluated in other medical procedures.

The terms "hyaluronan" or "hyaluronic acid" are used in literature to mean acidic polysaccharides with different molecular weights constituted by residues of D-glucuronic and N-acetyl-D-glucosamine acids, which occur naturally in cell surfaces, in the basic extracellular substances of the connective tissue of vertebrates, in the synovial fluid of the joints, in the endobulbar fluid of the eye, in human umbilical cord tissue and in cocks' combs.

The term "hyaluronic acid" is in fact usually used as meaning a whole series of polysaccharides with alternating residues of D-glucuronic and N-acetyl-D-glucosamine acids with varying molecular weights or even the degraded fractions of the same, and it would therefore seem more correct to use the plural term of "hyaluronic acids". The singular term will, however, be used all the same in this description; in addition, the abbreviation "HA" will frequently be used in place of this collective term.

HA plays an important role in the biological organism, as a mechanical support for the cells of many tissues, such as the skin, tendons, muscles and cartilage, it is a main component of the intercellular matrix. HA also plays other important parts in the biological processes, such as the moistening of tissues, and lubrication.

HA may be extracted from the above mentioned natural tissues, although today it is preferred to prepare it by microbiological methods to minimize the potential risk of transferring infectious agents, and to increase product uniformity, quality and availability.

HA and its various molecular size fractions and the respective salts thereof have been used as medicaments, especially in treatment of arthropathies, as an auxiliary and/or substitute agent for natural organs and tissues, especially in ophthalmology and cosmetic surgery, and as agents in cosmetic preparations. Products of hyaluronan have also been developed for use in orthopaedics, rheumatology, and dermatology.

HA may also be used as an additive for various polymeric materials used for sanitary and surgical articles, such as polyurethanes, polyesters etc. with the effect of rendering these materials biocompatible.

Water soluble gel forming materials comprising hyaluronic acid or salts thereof are well-known and used widely in the health care sector, e.g., in ophthalmology, in the treatment of osteoarthritis, as well as in the pharmaceutical and cosmetics industries. These materials are ideally sold, transported, and stored in a dried form. However, dried products comprising hyaluronic acid or salts thereof have been notoriously slowly dissolving.

The time it takes for a dried HA-product to be completely dissolved is an important parameter, especially in the health care industry, therefore it is of considerable interest to minimize the total dissolution time, i.e., the time it takes to disperse and solubilize a dried HA product. This invention is useful for manufacturing fast dissolving products of hyaluronic acid or salts thereof, and similar water soluble gel forming materials.

SUMMARY OF THE INVENTION

A problem to be solved by the present invention is how to provide a highly water-soluble dried HA product.

The present invention shows that agglomeration of a dried HA product greatly improves the solubility of the product, thus achieving very fast dissolution in an aqueous solvent, which preferably is water or saline water.

Accordingly, in a first aspect the invention relates to a product comprising hyaluronic acid or a salt thereof, which product is dried and agglomerated, preferably dried and agglomerated as disclosed herein.

In a second aspect, the invention relates to a composition comprising a product as defined in the first aspect, and an active ingredient, preferably the active ingredient is a pharmacologically active agent.

A third aspect of the invention relates to a pharmaceutical composition comprising an effective amount of a product as defined in the first aspect, together with a pharmaceutically acceptable carrier, excipient or diluent.

A fourth aspect relates to a pharmaceutical composition comprising an effective amount of a product as defined in the first aspect as a vehicle, together with a pharmacologically active agent.

A fifth aspect relates to a cosmetic article comprising as an active ingredient an effective amount of a product as defined in the first aspect or a composition as defined in any of the second, third, or fourth aspects.

In a sixth aspect, the invention relates to a sanitary, medical or surgical article comprising a product as defined in the first aspect or a composition as defined in any of the second, third, or fourth aspects, preferably the article is a diaper, a sanitary towel, a surgical sponge, a wound healing sponge, or a part comprised in a band aid or other wound dressing material.

An important aspect relates to a medicament capsule or microcapsule comprising a product as defined in the first aspect or a composition as defined in any of the second, third, or fourth aspects.

Another important aspect of the invention relates to a method of producing a dried and agglomerated product comprising hyaluronic acid or a salt thereof, the method comprising the steps of:

a) drying a product comprising hyaluronic acid or a salt thereof; and b) agglomerating the dried product.

Final aspects of the invention relate to methods of performing procedures in ophthalmology, in the treatment of osteoarthritis or cancer, hair loss or baldness, of treating a wound, of performing dermal or transdermal administration of a pharmacologically active agent, or dermal administration of a cosmetic, the improvement which comprises the use of a product as defined in the first aspect, or a composition as defined in any of the second, third, or fourth aspects.

A number of aspects relate to uses of a product as defined in any of claims 1-12 or a composition as defined in any of claims 13-16, for the manufacture of a medicament for the treatment of osteoarthritis, cancer, the manufacture of a medicament for an ophthalmological treatment, the manufacture of a medicament for the treatment of a wound, the manufacture of a medicament for angiogenesis, the manufacture of a medicament for the treatment of hair loss or baldness, or the manufacture of a moisturizer.

BRIEF DESCRIPTION OF THE FIGURES

FIG. 2, panel A, shows skin surface (stratum corneum), hair follicle and hair shaft; panel B clearly shows that green fluorescence from HA is primarily visible around and/or in the follicle.

FIG. 3, panel A, shows a skin surface; FIG. 3 panel B shows, that only limited fluorescence from labelled HA is visible on that surface.

FIG. 4, panel A, shows a skin surface (stratum corneum), hair follicle and hair shaft; panel B shows the green fluorescence from labelled HA around the follicle.

FIG. 5, panel A, shows a skin surface; panel B shows that while limited fluorescence from labelled HA is visible on that surface, it is accumulated between the keratinocytes.

DEFINITIONS

Nucleic Acid Constructs

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct may be synonymous with the term expression cassette when the nucleic acid construct contains all the control sequences required for expression of a coding sequence. The term "coding sequence" is defined herein as a sequence which is transcribed into mRNA and translated into an enzyme of interest when placed under the control of the below mentioned control sequences. The boundaries of the coding sequence are generally determined by a ribosome binding site located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

The techniques used to isolate or clone a nucleic acid sequence encoding a polypeptide are well known in the art and include, for example, isolation from genomic DNA, preparation from cDNA, or a combination thereof. The cloning of the nucleic acid sequences from such genomic DNA can be effected, e.g., by using antibody screening of expression libraries to detect cloned DNA fragments with shared structural features or the well known polymerase chain reaction (PCR). See, for example, Innis et al., 1990, PCR Protocols: A Guide to Methods and Application, Academic Press, New York. Other nucleic acid amplification procedures such as ligase chain reaction, ligated activated transcription, and nucleic acid sequence-based amplification may be used. The cloning procedures may involve excision and isolation of a desired nucleic acid fragment comprising the nucleic acid sequence encoding the polypeptide, insertion of the fragment into a vector molecule, and incorporation of the recombinant vector into a *Bacillus* cell where clones of the nucleic acid sequence will be replicated. The nucleic acid sequence may be of genomic, cDNA, RNA, semi-synthetic, synthetic origin, or any combinations thereof.

An isolated nucleic acid sequence encoding an enzyme may be manipulated in a variety of ways to provide for expression of the enzyme. Manipulation of the nucleic acid sequence prior to its insertion into a construct or vector may be desirable or necessary depending on the expression vector or *Bacillus* host cell. The techniques for modifying nucleic acid sequences utilizing cloning methods are well known in the art. It will be understood that the nucleic acid sequence may also be manipulated in vivo in the host cell using methods well known in the art.

A number of enzymes are involved in the biosynthesis of hyaluronic acid. These enzymes include hyaluronan synthase, UDP-glucose 6-dehydrogenase, UDP-glucose pyrophosphorylase, UDP-N-acetylglucosamine pyrophosphorylase, glucose-6-phosphate isomerase, hexokinase, phosphoglucomutase, amidotransferase, mutase, and acetyl transferase. Hyaluronan synthase is the key enzyme in the production of hyaluronic acid.

"Hyaluronan synthase" is defined herein as a synthase that catalyzes the elongation of a hyaluronic chain by the addition of GlcUA and GlcNAc sugar precursors. The amino acid sequences of *Streptococcal* hyaluronan synthases, vertebrate hyaluronan synthases, and the viral hyaluronan synthase are distinct from the *Pasteurella* hyaluronan synthase, and have been proposed for classification as Group I and Group II hyaluronan synthases, the Group I hyaluronan synthases including *Streptococcal* hyaluronan synthases (DeAngelis, 1999). For production of hyaluronan in *Bacillus* host cells, hyaluronan synthases of a eukaryotic origin, such as mammalian hyaluronan synthases, are less preferred.

The hyaluronan synthase encoding sequence may be any nucleic acid sequence capable of being expressed in a *Bacillus* host cell. The nucleic acid sequence may be of any origin. Preferred hyaluronan synthase genes include any of either Group I or Group II, such as the Group I hyaluronan synthase genes from *Streptococcus equisimilis, Streptococcus pyogenes, Streptococcus uberis*, and *Streptococcus equi* subsp. *zooepidemicus*, or the Group II hyaluronan synthase genes of *Pasturella multocida*.

Constructs whereby precursor sugars of hyaluronan are supplied to the host cell are preferably in producing the HA of the invention, either to the culture medium, or by being encoded by endogenous genes, by non-endogenous genes, or by a combination of endogenous and non-endogenous genes in the *Bacillus* host cell. The precursor sugar may be D-glucuronic acid or N-acetyl-glucosamine.

In the methods of the present invention, the nucleic acid construct may further comprise one or more genes encoding enzymes in the biosynthesis of a precursor sugar of a hyaluronan. Alternatively, the *Bacillus* host cell may further comprise one or more second nucleic acid constructs comprising one or more genes encoding enzymes in the biosynthesis of the precursor sugar. Hyaluronan production is improved by the use of constructs with a nucleic acid sequence or sequences encoding a gene or genes directing a step in the synthesis pathway of the precursor sugar of hyaluronan. By "directing a step in the synthesis pathway of a precursor sugar of hyaluronan" is meant that the expressed protein of the gene is active in the formation of N-acetyl-glucosamine or D-glucuronic acid, or a sugar that is a precursor of either of N-acetyl-glucosamine and D-glucuronic acid.

In a preferred method for supplying precursor sugars, constructs are provided for improving hyaluronan production in a host cell having a hyaluronan synthase, by culturing a host cell having a recombinant construct with a heterologous promoter region operably linked to a nucleic acid sequence encoding a gene directing a step in the synthesis pathway of a precursor sugar of hyaluronan. In a preferred method the host cell also comprises a recombinant construct having a promoter region operably linked to a hyaluronan synthase, which may use the same or a different promoter region than the nucleic acid sequence to a synthase involved in the biosynthesis of N-acetyl-glucosamine. In a further preferred embodiment, the host cell may have a recombinant construct with a promoter region operably linked to different nucleic acid sequences encoding a second gene involved in the synthesis of a precursor sugar of hyaluronan.

Thus, the present invention also relates to constructs for improving hyaluronan production by the use of constructs with a nucleic acid sequence encoding a gene directing a step in the synthesis pathway of a precursor sugar of hyaluronan. The nucleic acid sequence to the precursor sugar may be expressed from the same or a different promoter as the nucleic acid sequence encoding the hyaluronan synthase.

The genes involved in the biosynthesis of precursor sugars for the production of hyaluronic acid include a UDP-glucose 6-dehydrogenase gene, UDP-glucose pyrophosphorylase gene, UDP-N-acetylglucosamine pyrophosphorylase gene, glucose-6-phosphate isomerase gene, hexokinase gene, phosphoglucomutase gene, amidotransferase gene, mutase gene, and acetyl transferase gene.

In a cell containing a hyaluronan synthase, any one or combination of two or more of hasB, hasC and hasD, or the homologs thereof, such as the *Bacillus subtilis* tuaD, gtaB, and gcaD, respectively, as well as hasE, may be expressed to increase the pools of precursor sugars available to the hyaluronan synthase. The *Bacillus subtilis* genome is described in Kunst, et al., Nature 390, 249-256, "The complete genome sequence of the Gram-positive bacterium *Bacillus subtilis*" (20 Nov. 1997). In some instances, such as where the host cell does not have a native hyaluronan synthase activity, the construct may include the hasA gene.

The nucleic acid sequence encoding the biosynthetic enzymes may be native to the host cell, while in other cases heterologous sequence may be utilized. If two or more genes are expressed they may be genes that are associated with one another in a native operon, such as the genes of the HAS operon of *Streptococcus equisimilis*, which comprises hasA, hasB, hasC and hasD. In other instances, the use of some combination of the precursor gene sequences may be desired, without each element of the operon included. The use of some genes native to the host cell, and others which are exogenous may also be preferred in other cases. The choice will depend on the available pools of sugars in a given host cell, the ability of the cell to accommodate overproduction without interfering with other functions of the host cell, and whether the cell regulates expression from its native genes differently than exogenous genes.

As one example, depending on the metabolic requirements and growth conditions of the cell, and the available precursor sugar pools, it may be desirable to increase the production of N-acetyl-glucosamine by expression of a nucleic acid sequence encoding UDP-N-acetylglucosamine pyrophosphorylase, such as the hasD gene, the *Bacillus* gcaD gene, and homologs thereof. Alternatively, the precursor sugar may be D-glucuronic acid. In one such embodiment, the nucleic acid sequence encodes UDP-glucose 6-dehydrogenase. Such nucleic acid sequences include the *Bacillus* tuaD gene, the hasB gene of *Streptococcus*, and homologs thereof. The nucleic acid sequence may also encode UDP-glucose pyrophosphorylase, such as in the *Bacillus* gtaB gene, the hasC gene of *Streptococcus*, and homologues thereof.

In the methods of the present invention, the UDP-glucose 6-dehydrogenase gene may be a hasB gene or tuaD gene; or homologues thereof.

In the present invention it is envisioned that the hyaluronan synthase gene and the one or more genes encoding a precursor sugar are under the control of the same promoter. Alternatively, the one or more genes encoding a precursor sugar are under the control of the same promoter but a different promoter driving the hyaluronan synthase gene. A further alternative is that the hyaluronan synthase gene and each of the genes encoding a precursor sugar are under the control of different promoters. In a preferred embodiment, the hyaluronan synthase gene and the one or more genes encoding a precursor sugar are under the control of the same promoter.

The present invention also relates to a nucleic acid construct comprising an isolated nucleic acid sequence encoding a hyaluronan synthase operon comprising a hyaluronan synthase gene and a UDP-glucose 6-dehydrogenase gene, and optionally one or more genes selected from the group consisting of a UDP-glucose pyrophosphorylase gene, UDP-N-acetylglucosamine pyrophosphorylase gene, and glucose-6-phosphate isomerase gene.

In some cases the host cell will have a recombinant construct with a heterologous promoter region operably linked to a nucleic acid sequence encoding a gene directing a step in the synthesis pathway of a precursor sugar of hyaluronan, which may be in concert with the expression of hyaluronan synthase from a recombinant construct. The hyaluronan synthase may be expressed from the same or a different promoter region than the nucleic acid sequence encoding an enzyme involved in the biosynthesis of the precursor. In another preferred embodiment, the host cell may have a recombinant construct with a promoter region operably linked to a different nucleic acid sequence encoding a second gene involved in the synthesis of a precursor sugar of hyaluronan.

The nucleic acid sequence encoding the enzymes involved in the biosynthesis of the precursor sugar(s) may be expressed from the same or a different promoter as the nucleic acid sequence encoding the hyaluronan synthase. In the former sense, "artificial operons" are constructed, which may mimic the operon of *Streptococcus equisimilis* in having each hasA, hasB, hasC and hasD, or homologs thereof, or, alternatively, may utilize less than the full complement present in the *Streptococcus equisimilis* operon. The artificial operons" may also comprise a glucose-6-phosphate isomerase gene (hasE) as well as one or more genes selected from the group consisting of a hexokinase gene, phosphoglucomutase gene, amidotransferase gene, mutase gene, and acetyl transferase gene. In the artificial operon, at least one of the elements is heterologous to one other of the elements, such as the promoter region being heterologous to the encoding sequences.

In a preferred embodiment, the nucleic acid construct comprises hasA, tuaD, and gtaB. In another preferred embodiment, the nucleic acid construct comprises hasA, tuaD, gtaB, and gcaD. In another preferred embodiment, the nucleic acid construct comprises hasA and tuaD. In another preferred embodiment, the nucleic acid construct comprises hasA. In another preferred embodiment, the nucleic acid construct comprises hasA, tuaD, gtaB, gcaD, and hasE. In another preferred embodiment, the nucleic acid construct comprises hasA, hasB, hasC, and hasD. In another preferred embodiment, the nucleic acid construct comprises hasA, hasB, hasC, hasD, and hasE. Based on the above preferred embodiments, the genes noted can be replaced with homologs thereof.

In the methods of the present invention, the nucleic acid constructs comprise a hyaluronan synthase encoding sequence operably linked to a promoter sequence foreign to the hyaluronan synthase encoding sequence. The promoter sequence may be, for example, a single promoter or a tandem promoter.

"Promoter" is defined herein as a nucleic acid sequence involved in the binding of RNA polymerase to initiate transcription of a gene. "Tandem promoter" is defined herein as two or more promoter sequences each of which is operably linked to a coding sequence and mediates the transcription of the coding sequence into mRNA. "Operably linked" is defined herein as a configuration in which a control sequence, e.g., a promoter sequence, is appropriately placed at a position relative to a coding sequence such that the control sequence directs the production of a polypeptide encoded by the coding sequence. As noted earlier, a "coding sequence" is defined herein as a nucleic acid sequence which is transcribed into mRNA and translated into a polypeptide when placed under the control of the appropriate control sequences. The boundaries of the coding sequence are generally determined by a ribosome binding site located just upstream of the open reading frame at the 5' end of the mRNA and a transcription terminator sequence located just downstream of the open reading frame at the 3' end of the mRNA. A coding sequence can include, but is not limited to, genomic DNA, cDNA, semisynthetic, synthetic, and recombinant nucleic acid sequences.

In a preferred embodiment, the promoter sequences may be obtained from a bacterial source. In a more preferred embodiment, the promoter sequences may be obtained from a gram positive bacterium such as a *Bacillus* strain, e.g., *Bacillus agaradherens*, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis*; or a *Streptomyces* strain, e.g., *Streptomyces lividans* or *Streptomyces murinus*; or from a gram negative bacterium, e.g., *E. coli* or *Pseudomonas* sp.

Examples of suitable promoters for directing the transcription of a nucleic acid sequence in the methods of the present invention are the promoters obtained from the *E. coli* lac operon, *Streptomyces coelicolor* agarase gene (dagA), *Bacillus lentus* or *Bacillus clausii* alkaline protease gene (aprH), *Bacillus licheniformis* alkaline protease gene (subtilisin Carlsberg gene), *Bacillus subtilis* levansucrase gene (sacB), *Bacillus subtilis* alpha-amylase gene (amyE), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus thuringiensis* subsp. *tenebrionis* CryIIIA gene (cryIIIA) or portions thereof, prokaryotic beta-lactamase gene (Villa-Kamaroff et al., 1978, Proceedings of the National Academy of Sciences USA 75:3727-3731). Other examples are the promoter of the spo1 bacterial phage promoter and the tac promoter (DeBoer et al., 1983, Proceedings of the National Academy of Sciences USA 80:21-25). Further promoters are described in "Useful proteins from recombinant bacteria" in Scientific American, 1980, 242:74-94; and in Sambrook, Fritsch, and Maniatus, 1989, Molecular Cloning, A Laboratory Manual, 2d edition, Cold Spring Harbor, N.Y.

The promoter may also be a "consensus" promoter having the sequence TTGACA for the "−35" region and TATAAT for the "−10" region. The consensus promoter may be obtained from any promoter which can function in a *Bacillus* host cell.

The construction of a "consensus" promoter may be accomplished by site-directed mutagenesis to create a promoter which conforms more perfectly to the established consensus sequences for the "10" and "−35" regions of the vegetative "sigma A-type" promoters for *Bacillus* subtilis (Voskuil et al., 1995, Molecular Microbiology 17: 271-279).

In a preferred embodiment, the "consensus" promoter is obtained from a promoter obtained from the *E. coli* lac operon, *Streptomyces coelicolor* agarase gene (dagA), *Bacillus clausii* or *Bacillus lentus* alkaline protease gene (aprH), *Bacillus licheniformis* alkaline protease gene (subtilisin Carlsberg gene), *Bacillus subtilis* levansucrase gene (sacB), *Bacillus subtilis* alpha-amylase gene (amyE), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus thuringiensis* subsp. *tenebrionis* CryIIIA gene (cryIIIA) or portions thereof, or prokaryotic beta-lactamase gene spo1 bacterial phage promoter. In a more preferred embodiment, the "consensus" promoter is obtained from *Bacillus amyloliquefaciens* alpha-amylase gene (amyQ).

Widner, et al., U.S. Pat. Nos. 6,255,076 and 5,955,310, describe tandem promoters and constructs and methods for use in expression in *Bacillus* cells, including the short consensus amyQ promoter (also called scBAN). The use of the cryIIIA stabilizer sequence, and constructs using the sequence, for improved production in *Bacillus* are also described therein.

Each promoter sequence of the tandem promoter may be any nucleic acid sequence which shows transcriptional activity in the *Bacillus* cell of choice including a mutant, truncated, and hybrid promoter, and may be obtained from genes encoding extracellular or intracellular polypeptides either homologous or heterologous to the *Bacillus* cell. Each promoter sequence may be native or foreign to the nucleic acid sequence encoding the polypeptide and native or foreign to the *Bacillus* cell. The promoter sequences may be the same promoter sequence or different promoter sequences.

The two or more promoter sequences of the tandem promoter may simultaneously promote the transcription of the nucleic acid sequence. Alternatively, one or more of the promoter sequences of the tandem promoter may promote the transcription of the nucleic acid sequence at different stages of growth of the *Bacillus* cell.

In a preferred embodiment, the tandem promoter contains at least the amyQ promoter of the *Bacillus* amyloliquefaciens alpha-amylase gene. In another preferred embodiment, the tandem promoter contains at least a "consensus" promoter having the sequence TTGACA for the "−35" region and TATAAT for the "−10" region. In another preferred embodiment, the tandem promoter contains at least the amyL promoter of the *Bacillus licheniformis* alpha-amylase gene. In another preferred embodiment, the tandem promoter contains at least the cryIIIA promoter or portions thereof (Agaisse and Lereclus, 1994, Molecular Microbiology 13: 97-107).

In a more preferred embodiment, the tandem promoter contains at least the amyL promoter and the cryIIIA promoter. In another more preferred embodiment, the tandem promoter contains at least the amyQ promoter and the cryIIIA promoter. In another more preferred embodiment, the tandem promoter contains at least a "consensus" promoter having the sequence TTGACA for the "−35" region and TATAAT for the "−10" region and the cryIIIA promoter. In another more preferred embodiment, the tandem promoter contains at least two copies of the amyL promoter. In another more preferred embodiment, the tandem promoter contains at least two copies of the amyQ promoter. In another more preferred embodiment, the tandem promoter contains at least two copies of a "consensus" promoter having the sequence TTGACA for the "−35" region and TATAAT for the "−10" region. In another more preferred embodiment, the tandem promoter contains at least two copies of the cryIIIA promoter.

"An mRNA processing/stabilizing sequence" is defined herein as a sequence located downstream of one or more promoter sequences and upstream of a coding sequence to which each of the one or more promoter sequences are operably linked such that all mRNAs synthesized from each promoter sequence may be processed to generate mRNA transcripts with a stabilizer sequence at the 5' end of the transcripts. The presence of such a stabilizer sequence at the 5' end of the mRNA transcripts increases their half-life (Agaisse and Lereclus, 1994, supra, Hue et al., 1995, Journal of Bacteriology 177: 3465-3471). The mRNA processing/stabilizing sequence is complementary to the 3' extremity of a bacterial 16S ribosomal RNA. In a preferred embodiment, the mRNA processing/stabilizing sequence generates essentially single-size transcripts with a stabilizing sequence at the 5' end of the transcripts. The mRNA processing/stabilizing sequence is preferably one, which is complementary to the 3' extremity of a bacterial 16S ribosomal RNA. See, U.S. Pat. Nos. 6,255,076 and 5,955,310.

In a more preferred embodiment, the mRNA processing/stabilizing sequence is the *Bacillus thuringiensis* cryIIIA mRNA processing/stabilizing sequence disclosed in WO 94/25612 and Agaisse and Lereclus, 1994, supra, or portions thereof which retain the mRNA processing/stabilizing function. In another more preferred embodiment, the mRNA processing/stabilizing sequence is the *Bacillus subtilis* SP82 mRNA processing/stabilizing sequence disclosed in Hue et al., 1995, supra, or portions thereof which retain the mRNA processing/stabilizing function.

When the cryIIIA promoter and its mRNA processing/stabilizing sequence are employed in the methods of the present invention, a DNA fragment containing the sequence disclosed in WO 94/25612 and Agaisse and Lereclus, 1994, supra, or portions thereof which retain the promoter and mRNA processing/stabilizing functions, may be used. Furthermore, DNA fragments containing only the cryIIIA promoter or only the cryIIIA mRNA processing/stabilizing sequence may be prepared using methods well known in the art to construct various tandem promoter and mRNA processing/stabilizing sequence combinations. In this embodiment, the cryIIIA promoter and its mRNA processing/stabilizing sequence are preferably placed downstream of the other promoter sequence(s) constituting the tandem promoter and upstream of the coding sequence of the gene of interest.

The isolated nucleic acid sequence encoding the desired enzyme(s) involved in hyaluronic acid production may then be further manipulated to improve expression of the nucleic acid sequence. Expression will be understood to include any step involved in the production of the polypeptide including, but not limited to, transcription, post-transcriptional modification, translation, post-translational modification, and secretion. The techniques for modifying nucleic acid sequences utilizing cloning methods are well known in the art.

A nucleic acid construct comprising a nucleic acid sequence encoding an enzyme may be operably linked to one or more control sequences capable of directing the expression of the coding sequence in a *Bacillus* cell under conditions compatible with the control sequences.

The term "control sequences" is defined herein to include all components which are necessary or advantageous for expression of the coding sequence of a nucleic acid sequence. Each control sequence may be native or foreign to the nucleic acid sequence encoding the enzyme. In addition to promoter sequences described above, such control sequences include, but are not limited to, a leader, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding an enzyme.

The control sequence may also be a suitable transcription terminator sequence, a sequence recognized by a *Bacillus* cell to terminate transcription. The terminator sequence is operably linked to the 3' terminus of the nucleic acid sequence encoding the enzyme or the last enzyme of an operon. Any terminator which is functional in the *Bacillus* cell of choice may be used in the present invention.

The control sequence may also be a suitable leader sequence, a nontranslated region of a mRNA which is important for translation by the *Bacillus* cell. The leader sequence is operably linked to the 5' terminus of the nucleic acid sequence encoding the enzyme. Any leader sequence which is functional in the *Bacillus* cell of choice may be used in the present invention.

The control sequence may also be a signal peptide coding region, which codes for an amino acid sequence linked to the amino terminus of a polypeptide which can direct the expressed polypeptide into the cell's secretory pathway. The signal peptide coding region may be native to the polypeptide or may be obtained from foreign sources. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide relative to the natural signal peptide coding region normally associated with the coding sequence. The signal peptide coding region may be obtained from an amylase or a protease gene from a *Bacillus* species. However, any signal peptide coding region capable of directing the expressed polypeptide into the secretory pathway of a *Bacillus* cell of choice may be used in the present invention.

An effective signal peptide coding region for *Bacillus* cells is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* prsA gene. Further signal peptides are described by Simonen and Palva, 1993, Microbiological Reviews 57:109-137.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE) and *Bacillus subtilis* neutral protease (nprT).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems.

Production

In the methods of the present invention, the host cells are cultivated in a nutrient medium suitable for production of the hyaluronic acid using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the enzymes involved in hyaluronic acid synthesis to be expressed and the hyaluronic acid to be isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted hyaluronic acid can be recovered directly from the medium.

The resulting hyaluronic acid may be isolated by methods known in the art. For example, the hyaluronic acid may be isolated from the nutrient medium by conventional procedures including, but not limited to, centrifugation, filtration, extraction, spray-drying, evaporation, or precipitation. The isolated hyaluronic acid may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., Protein Purification, J.-C. Janson and Lars Ryden, editors, VCH Publishers, New York, 1989).

DETAILED DESCRIPTION OF THE INVENTION

Hyaluronic Acid

"Hyaluronic acid" is defined herein as an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. The terms hyaluronan and hyaluronic acid are used interchangeably herein.

Rooster combs are a significant commercial source for hyaluronan. Microorganisms are an alternative source. U.S. Pat. No. 4,801,539 discloses a fermentation method for preparing hyaluronic acid involving a strain of *Streptococcus zooepidemicus* with reported yields of about 3.6 g of hyaluronic acid per liter. European Patent No. EP0694616 discloses fermentation processes using an improved strain of

*Streptococcus zooepidemicus* with reported yields of about 3.5 g of hyaluronic acid per liter. As disclosed in WO 03/054163 (Novozymes), which is incorporated herein in its entirety, hyaluronic acid or salts thereof may be recombinantly produced, e.g., in a Gram-positive *Bacillus* host.

Hyaluronan synthases have been described from vertebrates, bacterial pathogens, and algal viruses (DeAngelis, P. L., 1999, *Cell. Mol. Life Sci.* 56: 670-682). WO 99/23227 discloses a Group I hyaluronate synthase from *Streptococcus equisimilis*. WO 99/51265 and WO 00/27437 describe a Group II hyaluronate synthase from *Pasturella multocida*. Ferretti et al. disclose the hyaluronan synthase operon of *Streptococcus pyogenes*, which is composed of three genes, hasA, hasB, and hasC, that encode hyaluronate synthase, UDP glucose dehydrogenase, and UDP-glucose pyrophosphorylase, respectively (*Proc. Natl. Acad. Sci. USA.* 98, 46584663, 2001). WO 99/51265 describes a nucleic acid segment having a coding region for a *Streptococcus equisimilis* hyaluronan synthase.

Since the hyaluronan of a recombinant *Bacillus* cell is expressed directly to the culture medium, a simple process may be used to isolate the hyaluronan from the culture medium. First, the *Bacillus* cells and cellular debris are physically removed from the culture medium. The culture medium may be diluted first, if desired, to reduce the viscosity of the medium. Many methods are known to those skilled in the art for removing cells from culture medium, such as centrifugation or microfiltration. If desired, the remaining supernatant may then be filtered, such as by ultrafiltration, to concentrate and remove small molecule contaminants from the hyaluronan. Following removal of the cells and cellular debris, a simple precipitation of the hyaluronan from the medium is performed by known mechanisms. Salt, alcohol, or combinations of salt and alcohol may be used to precipitate the hyaluronan from the filtrate. Once reduced to a precipitate, the hyaluronan can be easily isolated from the solution by physical means. The hyaluronan may be dried or concentrated from the filtrate solution by using evaporative techniques known to the art, such as spray drying.

The first aspect of the invention relates to a product comprising hyaluronic acid or a salt thereof, which product is dried and agglomerated as defined herein.

Host Cells

A preferred embodiment relates to the product of the first aspect, wherein the hyaluronic acid or salt thereof is recombinantly produced, preferably by a Gram-positive bacterium or host cell, more preferably by a bacterium of the genus *Bacillus*.

The host cell may be any *Bacillus* cell suitable for recombinant production of hyaluronic acid. The *Bacillus* host cell may be a wild-type *Bacillus* cell or a mutant thereof. *Bacillus* cells useful in the practice of the present invention include, but are not limited to, *Bacillus agaraderhens, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells. Mutant *Bacillus subtilis* cells particularly adapted for recombinant expression are described in WO 98/22598. Non-encapsulating *Bacillus* cells are particularly useful in the present invention.

In a preferred embodiment, the *Bacillus* host cell is a *Bacillus amyloliquefaciens, Bacillus clausii, Bacillus lentus, Bacillus licheniformis, Bacillus stearothermophilus* or *Bacillus subtilis* cell. In a more preferred embodiment, the *Bacillus* cell is a *Bacillus amyloliquefaciens* cell. In another more preferred embodiment, the *Bacillus* cell is a *Bacillus clausii* cell. In another more preferred embodiment, the *Bacillus* cell is a *Bacillus lentus* cell. In another more preferred embodiment, the *Bacillus* cell is a *Bacillus licheniformis* cell. In another more preferred embodiment, the *Bacillus* cell is a *Bacillus subtilis* cell. In a most preferred embodiment, the *Bacillus* host cell is *Bacillus subtilis* A164Δ5 (see U.S. Pat. No. 5,891,701) or *Bacillus subtilis* 168Δ4.

Transformation of the *Bacillus* host cell with a nucleic acid construct of the present invention may, for instance, be effected by protoplast transformation (see, e.g., Chang and Cohen, 1979, Molecular General Genetics 168: 111-115), by using competent cells (see, e.g., Young and Spizizen, 1961, Journal of Bacteriology 81: 823-829, or Dubnau and Davidoff-Abelson, 1971, Journal of Molecular Biology 56: 209-221), by electroporation (see, e.g., Shigekawa and Dower, 1988, Biotechniques 6: 742-751), or by conjugation (see, e.g., Koehler and Thorne, 1987, Journal of Bacteriology 169: 5271-5278).

Molecular Weight

The level of hyaluronic acid may be determined according to the modified carbazole method (Bitter and Muir, 1962, *Anal Biochem.* 4: 330-334). Moreover, the average molecular weight of the hyaluronic acid may be determined using standard methods in the art, such as those described by Ueno et al., 1988, *Chem. Pharm. Bull.* 36: 4971-4975; Wyatt, 1993, *Anal. Chim. Acta* 272: 140; and Wyatt Technologies, 1999, "Light Scattering University DAWN Course Manual" and "DAWN EOS Manual" Wyatt Technology Corporation, Santa Barbara, Calif.

In a preferred embodiment, the hyaluronic acid obtained by the methods of the present invention has a molecular weight of about 10,000 to about 10,000,000 Da. In a more preferred embodiment, the hyaluronic acid obtained by the methods of the present invention has a molecular weight of about 25,000 to about 5,000,000 Da. In a most preferred embodiment, the hyaluronic acid obtained by the methods of the present invention has a molecular weight of about 50,000 to about 3,000,000 Da.

A preferred embodiment relates to the product of the first aspect, wherein the hyaluronic acid or salt thereof has a molecular weight in the range of between 300,000 and 3,000,000; preferably in the range of between 400,000 and 2,500,000; more preferably in the range of between 500,000 and 2,000,000; and most preferably in the range of between 600,000 and 1,800,000 Da.

Where recombinantly produced hyaluronic acid or salt thereof is used in the methods of the invention to manufacture the products or compositions of the invention, it may be advantageous for some applications to first reduce the average molecular weight of the hyaluronic acid or salt thereof. For instance, it has been stated by several manufacturers of so-called low-molecular weight fractions of hyaluronic acid, that it is capable of penetrating the skin barrier to reestablish the natural content of hyaluronic acid in the skin, therefore such fractions are particularly suitable for cosmetic compositions sold as anti-skin-ageing and anti-wrinkle agents. For food applications, low MW hyaluronic acid has been shown to penetrate the gastrointestinal barrier, thereby increasing its bioavailability. Finally, low MW hyaluronic acid exhibits anti-inflammatory effect and have potential applications in the treatment of inflammatory diseases. A reduction of the average molecular weight of a hyaluronic acid or salt thereof may be achieved by standard methods in the art, such as, simple heat treatment, enzymatic degradation, ultrasound sonication, or acid hydrolysis. See, e.g., U.S. Pat. No. 6,020,484, which describes an ultrasonication technique of HA including NaOCl as additive, and T. Miyazaki et al. (2001) Polymer Degradation and Stability, 74: 77-85.

Accordingly, a preferred embodiment relates to the product of the first aspect, wherein the hyaluronic acid or salt thereof has a low average molecular weight in the range of between 10,000 and 800,000 Da; preferably in the range of between 20,000 and 600,000 Da; more preferably in the range of between 30,000 and 500,000 Da; even more preferably in the range of between 40,000 and 400,000 Da; and most preferably in the range of between 50,000 and 300,000 Da.

Salts and Crosslinked HA

A preferred embodiment relates to a product of the first aspect, which comprises an inorganic salt of hyaluronic acid, preferably sodium hyaluronate, potassium hyaluronate, ammonium hyaluronate, calcium hyaluronate, magnesium hyaluronate, zinc hyaluronate, or cobalt hyaluronate.

The preparation of a crosslinked HA or salt thereof, which is prepared by crosslinking HA with a polyfunctional epoxy compound is disclosed in EP 0 161 887 B1. Total or partial crosslinked esters of HA with an aliphatic alcohol, and salts of such partial esters with inorganic or organic bases, are disclosed in U.S. Pat. No. 4,957,744. Other ways of crosslinking HA are disclosed in U.S. Pat. Nos. 5,616,568, 5,652,347, and 5,874,417. Crosslinked HA may also be prepared by treating HA with boric acid, as follows:

Dried sodium hyaluronate (Na-HA, 203 mg), recombinantly produced in a *Bacillus subtilis* by fermentation (WO 03/054163; Novozymes), was dissolved into 0.2 M NaOH to give a 4% solution. Boric acid (35 mg (approx. 1 equivalent of HA disaccharide) was added and the sample was stirred at room temperature for 1.5 h, and then stored at 5° C. for ca. 2.5 days. A control sample was prepared in parallel exactly as described above, but without boric acid.

The viscosity of the resulting HA-borate hydrogel was measured at 25° C. using a Carrimed CSL controlled stress rheometer (cone geometry: 6 cm, 2°). The viscosity depended on the shear rate and increased at least 4-fold (from 4.2- to 8.4 fold) in the HA-borate hydrogel as compared to the control sample, indicating formation of a cross-linked network.

New peaks at 1200 and 945 cm-1 were observed on the FT-IR spectrum of the HA-borate hydrogel, when compared to a standard spectrum of Na-HA, corresponding to the presence of newly formed borate esters in the crosslinked HA-borate hydrogel.

Accordingly, a preferred embodiment relates to the product of the first aspect, which comprises crosslinked hyaluronic acid or salt thereof, preferably the hyaluronic acid is crosslinked with boric acid, and more preferably the crosslinked hyaluronic acid comprises borate esters.

Determination of Moisture

The moisture content of a dried product powder according to the invention is the loss in weight, expressed as a percentage, after drying the powder at 102° C.±2° C. to a constant weight. An empty glass weighing dish with a ground lid is dried in the oven, then cooled and weighed on an analytical balance with a sensitivity of at least 0.1 mg. Approximately 3 g dried product powder is placed in the dish and weighed. The dish with the powder is placed without the lid in the oven and dried for 2 hours at a temperature of 102° C.±2° C.; then it is placed in a desiccator and cooled to room temperature before it is weighed again. The dish with the powder is placed without the lid in the oven to dry for 1 more hour, and then cooled and weighed as already described; this is repeated until the weight remains constant, i.e., until two successive weighings do not differ by more than 0.5 mg.

The percentage of moisture is then calculated as: (W2−W3)/(W2−W1)×100; where W1 is the weight of the empty dish, W2 is the weight of the dish with powder, and W3 is the weight of the dish with dried powder. The result is calculated to 2 decimal places, and the reproducibility of this method is about ±0.1%.

Preferably, the dried and agglomerated product of the first aspect, comprises less than 5% moisture, preferably less than 2%, and most preferably less than 1% moisture, as determined herein.

Particle Size

A preferred product of the first aspect has a particle size the 50 percentile of which, $D_{50}$, is between 10 and 1,000 microns, preferably between 100 and 1,000 microns, more preferably between 150 and 900 microns, and even more preferably between 200 and 800 microns, as determined by laser diffraction measurement of the particles suspended in isopropanol, as shown in the examples below.

In a preferred embodiment, the polydispersity of a product of the first aspect is measured as the SPAN value, which is calculated according to the following formula: SPAN=$(D_{90}-D_{10})/D_{50}$, and the SPAN value is between 1.0 and 2.5; preferably the SPAN value is between 1.2 and 2.2; more preferably the SPAN value is between 1.5 and 1.9; and most preferably the SPAN value is between 1.6 and 1.8.

Dispersibility

The dispersibility of the product of the invention is determined as follows: 0.1 g of the dried and agglomerated product is added to a 100 ml glass bottle. 50 ml of a 0.9% (w/v) sodium chloride solution is added and the bottle is sealed and inverted 180 degrees by hand repeatedly until all particles added are dispersed as single particles, i.e., until no lumps are left, as determined by visual inspection, and record the time taken to perform the inversions on a data sheet. The time thus recorded is the dispersibility of the product.

A preferred product of the first aspect has a dispersibility of less than 30 minutes in an aqueous solvent, which preferably is water, preferably less than 20 minutes, more preferably less than 15 minutes, more preferably less than 10 minutes, more preferably less than 5 minutes, more preferably less than 3 minutes, more preferably less than 2 minutes, and most preferably less than 1 minute, as determined herein.

Solubility

The solubility in various solvents of a dried, or dried and aggregated, product or composition comprising hyaluronic acid according to the invention may be determined as follows:

Add 0.1 g of the hyaluronan powder to be tested to a 100 ml sealable glass flask. The add 50 ml of 0.9% (w/v) sodium chloride, injection grade water, absolute ethanol, acetone or ether to the flask containing the HA sample to be tested. Seal the flask and perform 180 degrees inversions by hand until the HA goes into solution, as determined by visual inspection, and record the time taken to perform the inversions on a data sheet. The time recorded is the solubility of the sample.

A preferred product according to the first aspect has a solubility of less than 60 minutes in an aqueous solvent, preferably less than 45 minutes, more preferably less than 40 minutes, even more preferably less than 35 minutes, 30 minutes, 25 minutes, 20 minutes, 15 minutes, 10 minutes, and most preferably less than 5 minutes, as determined herein.

Other Ingredients

In a preferred embodiment, the dried and agglomerated product of the invention may also comprise other ingredients, preferably one or more active ingredient, preferably one or more pharmacologically active substance, and also preferably a water-soluble excipient, such as lactose.

Non-limiting examples of an active ingredient or pharmacologically active substance which may be used in the present invention include protein and/or peptide drugs, such as, human growth hormone, bovine growth hormone, porcine growth hormone, growth hormone releasing hormone/peptide, granulocyte-colony stimulating factor, granulocyte macrophage-colony stimulating factor, macrophage-colony stimulating factor, erythropoietin, bone morphogenic protein, interferon or derivative thereof, insulin or derivative thereof, atriopeptin-III, monoclonal antibody, tumor necrosis factor, macrophage activating factor, interleukin, tumor degenerating factor, insulin-like growth factor, epidermal growth factor, tissue plasminogen activator, factor IIV, factor IIIV, and urokinase.

A water-soluble excipient my be included for the purpose of stabilizing the active ingredient(s), such excipient may include a protein, e.g., albumin or gelatin; an amino acid, such as glycine, alanine, glutamic acid, arginine, lysine and a salt thereof; carbohydrate such as glucose, lactose, xylose, galactose, fructose, maltose, saccharose, dextran, mannitol, sorbitol, trehalose and chondroitin sulphate; an inorganic salt such as phosphate; a surfactant such as TWEEN® (ICI), poly ethylene glycol, and a mixture thereof. The excipient or stabilizer may be used in an amount ranging from 0.001 to 99% by weight of the product.

Several aspects of the invention relate to various compositions and pharmaceutical comprising, a month other constituents, an effective amount of the product as defined in the first aspect, and an active ingredient, preferably the active ingredient is a pharmacologically active agent; a pharmaceutically acceptable carrier, excipient or diluent, preferably a water-soluble excipient, and most preferably lactose.

A preferred embodiment of the invention relates to products or compositions of the invention comprised in an effervescent tablet, which may otherwise be formulated as described in the art. For instance, an effervescent tablet may comprise citric acid, sodium bicarbonate, and an oligosaccharide or other sugar. Effervescent tablets are easy to store, and with the fast-dissolving product of the present invention, they are quickly dissolved and thus provide an ideal means of oral administration.

In addition, aspects of the invention relate to articles comprising a product as defined in the first aspect or a composition as defined in the aspects and embodiments above, e.g., a cosmetic article, a sanitary article, a medical or surgical article. In a final aspect the invention relates to a medicament capsule or microcapsule comprising a product as defined in the first aspect or a composition as defined in other aspects and embodiments of the invention.

Method of Production

The present invention in another aspect provides a method of producing a product as defined in the first aspect of the invention and/or preferred embodiments thereof, the method comprising the steps of:

a) drying a product comprising hyaluronic acid or a salt thereof; and b) agglomerating the dried product.

Spray Drying and Agglomerating

In a preferred embodiment of the method, the drying step is done using a spray-dryer, preferably a Two-Fluid-Nozzle (TFN) or a Rotary Atomizer, and preferably the spray-drying was done using a TFN and the following condition ranges:

| | |
|---|---|
| Inlet temperature: | 100-200° C. |
| Outlet temperature: | 40-90° C. |
| Nozzle atomization pressure: | 2-10 bar |
| Nozzle air temperature: | 40-100° C. |
| Feed temperature: | 40-100° C. |

Another preferred embodiment relates to the method above, wherein the agglomerating step is done using a fluidized bed; preferably wherein the fluidized bed inlet temperature is in the range of 30-80° C., and wherein the aqueous solution of the powder is sprayed on the dried powder at a rate corresponding to an outlet temperature of 25-50° C.

Yet another preferred embodiment relates to the method above, wherein the agglomerating step is done using a water-solvent mixture, preferably having a water-solvent ratio of between 0:100 and 50:50, and more preferably having a water:solvent ratio of between 0:100 and 20:80; preferably the solvent is an alcohol, and more preferably the solvent is iso-propanol.

It is preferred that the drying and agglomerating is done in one step, preferably using a fluidized spray-dryer.

Methods of Using the Product or Composition

Various aspects of the invention relate to methods of performing treatment procedures, e.g., in the medical field, using a product of the first aspect, or using compositions of the invention.

One aspect relates to a method of performing procedures in ophthalmology, which comprises the use of a product as defined in the first aspect or a composition of the invention.

Another aspect relates to a method of performing procedures in the treatment of osteoarthritis, which comprises the use of a product as defined in the first aspect or a composition of the invention.

Yet another aspect relates to a method of performing procedures in the treatment of cancer, which comprises the use of a product as defined in the first aspect or a composition of the invention.

Still another aspect relates to a method of performing procedures in the treatment of hair loss or baldness, the improvement which comprises the use of a product as defined in the first aspect or a composition of the invention.

An aspect relates to a method of performing transdermal or dermal administration of a pharmacologically active agent, which comprises the use of a product as defined in the first aspect or a composition of the invention.

Another aspect relates to a method of performing dermal administration of a cosmetic, which comprises the use of a product as defined in the first aspect or a composition of the invention.

An aspect relates to an ophthamological method of using a product as defined in the first aspect or a composition of the invention.

Another aspect relates to a method of treating osteoarthritis, comprising administering an effective amount of a product as defined in the first aspect or a composition of the invention to a mammal, preferably the administering is dermal, transdermal, oral, or by injection.

An aspect relates to a method of treating a wound, comprising administering an effective amount of a product as defined in the first aspect or a composition of the invention to a mammal.

Still another aspect relates to a method of treating hair loss or baldness, comprising administering an effective amount of a product as defined in the first aspect or a composition of the invention to a mammal, preferably the administering is dermal, transdermal, oral, or by injection.

Other aspects relate to the use of a product as defined in the first aspect or a composition of the invention for the manufacture of a medicament for the treatment of osteoarthritis, a medicament for an ophthalmological treatment, a medicament for the treatment of cancer, a medicament for the treatment of a wound, a medicament for angiogenesis, or a medicament for the treatment of hair loss or baldness.

A final aspect relates to the use of a product as defined in the first aspect or a composition of the invention for the manufacture of a moisturizer.

EXAMPLES

Example 1

A liquid feed consisting of Sodium Hyaluronate solution containing about 8 g/litre was spray dried using two different types of atomization techniques: A) Two-Fluid-Nozzle (TFN) and B) Rotary Atomizer. Commercially available types of spray-drying techniques and equipment are envisioned as being suitable for the purposes of this invention also (See e.g. Niro Atomizers Inc).

The resulting dried powders were noticeable different. The powder produced by the TFN had a significantly smaller bulk density. The reason for this difference was revealed upon further analysis shown below.

| Atomizer (batch no.) | Particle Density (g/ml) | Solubility Time (min) | Particle Size ($D_{50}$) |
|---|---|---|---|
| A) TFN (04PBAC0016) | 0.210 | 15 | 95 |
| B) Rotary Atomizer (MAG30012) | 0.430 | 31 | 45 |

It was seen that the solubility time was significantly decreased using the TFN atomization principle, as compared to the rotary atomizer. Despite the fact that the particle size was much bigger, which normally would lead to increased solubility time. The decreased solubility time was, however, found to be due to included air in the TFN spray dried particles. This could be seen from the particle density of the TFN product, which was less than half of that of the dried product produced by the rotary atomizer.

Example 2

A liquid feed preparation consisting of 75,000 g Sodium Hyaluronate solution, with about 8 g/liter Sodium Hyaluronate and 2400 g sodium chloride was added to a spray dryer at constant rate. The Hyaluronate had a molecular weight of about 690.000 Da. The spray dryer had a diameter of about 1.8 m and a height of about 5 m. A Two-Fluid-Nozzle (TFN) was selected for the atomization of the feed. The drying conditions were adjusted to give a dry powder batch (batch nr. 03PBAC0035-1) with the desired particle size:

| Inlet temperature: | 160° C. |
|---|---|
| Outlet temperature: | 75° C. |
| Nozzle atomization pressure: | 4 bar |
| Nozzle air temperature: | 70° C. |
| Feed temperature: | 60° C. |

The resulting particle size distribution was measured using laser diffraction on a suspension of the powder in isopropanol:

| $D_{10}$: | 12 microns |
|---|---|
| $D_{50}$: | 39 microns |
| $D_{90}$: | 84 microns |

Molecular weight: 631.000 Da
SPAN: 1.77

A measure of the polydispersity is the 'SPAN' value, which may be calculated according to the following formula:

$$SPAN=(D_{90}-D_{10})/D_{50}$$

The molecular weight was nearly unchanged during the drying operation, thus demonstrating the spray drying process to be very gentle despite the high temperatures applied.

Example 3

5 g samples of the spray-dried powder manufactured in Example 2 was agglomerated by suspending powder samples in 20 ml of each of the following solvent-water mixtures:
100% isopropanol (IPA)
90% isopropanol
87% isopropanol The suspensions were subsequently filtered and dried in vacuum. The dried filter cakes were crushed and screened through sieves to remove all particles below 150 microns and larger than 600 microns.

It was surprisingly found that the agglomerated particles thus manufactured were very fast dispersing and dissolving in saline. To investigate this phenomenon, the particle size was measured more accurately using laser diffraction on a suspension of the product in pure IPA. The particle sizes thus determined (10, 50, and 90 percentiles) are shown in table 1 below. A significant increase in the average agglomerated particle size was observed, as the water content in the solvent-water mixture used for agglomeration was increased from 0 to 13%.

TABLE 1

| Particle size | D(v, 0.1) micron | D(v, 0.5) Micron | D (v, 0.9) micron |
|---|---|---|---|
| 100% IPA | 14 | 60 | 242 |
| 90% IPA | 20 | 71 | 505 |
| 87% IPA | 21 | 179 | 538 |

In order to achieve a sufficiently fast dispersion it was found that the particle size should be above approximately 180 micron. Consequently, a sieve fraction from 180-355 micron of the batch which was agglomerated using 87% IPA was prepared. This fraction was subsequently compared to the non-agglomerated but otherwise identical product from Example 2. The results are shown in table 2 below. Clearly, the solubility time is significantly improved by the agglomeration process.

TABLE 2

| Batch (treatment) | Dispersion time sec | Solubility time min |
|---|---|---|
| 03PBAC0035 (Non agglomerated) | >1 minute | 14.0 |
| 03PBAC0035 (Agglomerated, 87% IPA) | <1 sec | 2.5 |

Example 4

The method described in Example 3 was used to treat the two batches described in Example 1 to see if it would be possible to modify the solubility time of a pure hyaluronate product. In table 3 below the results are shown for a sieve fraction of 250-500 micron for the agglomerated products. It is clearly seen that the solubility time may be significantly reduced by combining the methods of Example 1 and 3.

TABLE 3

| Atomizer (batch no.) | Solubility Time, Non agglomerated (min) | Solubility Time agglomerated (min) |
|---|---|---|
| A) TFN (04PBAC0016) | 15 | 9 |
| B) Rotary Atomizer (MAG30012) | 31 | 17 |

Example 5

The powder manufactured in Example 1 was treated in following way: About 100 g dried powder was added to a Strea laboratory fluid bed. The inlet temperature was 55° C. A 1% aqueous solution of the powder manufactured in Example 1 was then sprayed on the dried powder at a rate corresponding to an outlet temperature of 35° C. The resulting formed agglomerates were tested for solubility, and they showed a remarkably improved solubility when compared to the untreated powder.

Example 6

A liquid feed preparation consisting of 75,000 g Sodium Hyaluronate solution and 2,400 g sodium chloride were added to a fluidized spray dryer (FSD) at constant rate. The FSD spray dryer was equipped with an integrated fluid-bed placed beneath the spray drying tower. The drying air with entrained fines was removed through the spray dryer roof and subsequently passed trough a cyclone that removed the particles. The removed particles were pneumatically transported back to the spray dryer where they were injected into the nozzle cloud.

The Hyaluronate had a molecular weight of 800 kDa and a concentration of about 8 g/liter. The spray dryer had a diameter of about 1.8 m and a height of about 5 m. The drying conditions were adjusted to give a dry powder batch (batch nr. 04PBAC0014) with the desired particle size:

| Inlet temperature: | 160° C. |
|---|---|
| Outlet temperature: | 68° C. |
| Nozzle atomization pressure: | 3.5 bar |
| Nozzle air temperature: | 50° C. |
| Feed temperature: | 60° C. |

Subsequently, particle size distribution was measured using laser diffraction on a suspension of the powder in isopropanol:

| $D_{10}$: | 89 micron |
|---|---|
| $D_{50}$: | 220 micron |
| $D_{90}$: | 466 micron |

Molecular weight: 796 kDa
Hyaluronate concentration: 493 mg/g

It is seen, that the molecular weight was nearly unchanged by the drying operation, thus demonstrating that the spray-drying process is very gentle despite the high temperatures applied.

The product fraction between 250 and 500 micron was tested for its dispersibility/solubility, as shown in table 4, and it was found to disperse and dissolve in about 2 minutes, which was much faster than the 15 minutes observed with the non-agglomerated spray dried product. The absorbance of the resulting solution was also measured at 600 nm to assure that no minute particles were remaining in the solution (table 4).

TABLE 4

| Atomizer (batch no.) | Solubility Time (min) | Absorbance $A_{600\,nm}$ |
|---|---|---|
| TFN (04PBAC0014) | 2 | 0.005 |

Example 7

Molecular Weight and Skin Penetration

Skin permeation of four different average molecular weight fractions of radiolabeled hyaluronic acid was investigated, using side-by-side diffusion cells with a diameter of 2 cm (effective skin area of 3.14 cm$^2$). The volume of the receptor phase was between 8 and 8.5 ml, and the volume of the donor compartment was between 1 and 1.5 ml.

Dermatomed skin (750 micrometer) from the porcine ear was thawed and placed on one side of the diffusion cell. Any noticeable hairs were carefully clipped with scissors. The other side of the diffusion cell was closed with a silicon disc. The receptor was filled with phosphate-buffered saline (PBS) at pH 7.4. A magnetic stir-bar was introduced.

Three 10 microliter samples of the donor phase (as provided with a cold/hot ratio of 5.64 mg/ml cold to 22.56 microgram/ml hot) were taken to determine the specific activity. The donor phases were then filled with the solution provided: for 5 ml (the volume received), only 3 or 4 cells could be set up.

The cells were placed on a stirrer plate and the experiment performed at ambient temperature. After 5 hours, the entire receptor phase was withdrawn and the radioactivity therein was determined by liquid scintillation counting. The receptor chamber was then re-filled with PBS and diffusion was allowed to proceed overnight.

After 22 hours (i.e., 5 hr+17 hr), the receiver solution was again withdrawn and analyzed for radioactivity. The cells were disassembled and the skin was incubated with 5 ml of SOLUENE® (PerkinElmer) for 48 hours, or until completely dissolved, before adding scintillation fluid and counting for radioactivity. The experimental results are summarized for the four different molecular weight HA fractions in Table 5.

TABLE 5

Summary of results from experiments examining the permeation of radiolabeled HA across excised porcine ear skin in vitro after 5 hours (5 h) and 22 hours (22 h).

| | HA 1500 KDa (ng/cm2) | HA 800 KDa (ng/cm2) | HA 300 KDa (ng/cm2) | HA 50 KDa (ng/cm2) |
|---|---|---|---|---|
| R1.5h | 14.1 | 38.7 | 168.7 | 524.2 |
| R2.5h | 10.4 | 20.8 | 62.9 | 171.1 |
| R3.5h | 18.8 | 50.3 | 101.0 | |
| R4.5h | | | 63.4 | |
| Average | 14.4 | 36.6 | 99.0 | 347.6 |
| Variation | 4.2 | 14.9 | 49.8 | 249.7 |
| Average Flux | 2.9 | 7.3 | 19.8 | 69.5 |

TABLE 5-continued

Summary of results from experiments examining the permeation of radiolabeled HA across excised porcine ear skin in vitro after 5 hours (5 h) and 22 hours (22 h).

| | HA 1500 KDa (ng/cm2) | HA 800 KDa (ng/cm2) | HA 300 KDa (ng/cm2) | HA 50 KDa (ng/cm2) |
|---|---|---|---|---|
| in (ng/cm2/h) | 0.8 | 3.0 | 10.0 | 49.9 |
| R1.22h | 77.4 | 233.2 | 733.3 | 2669.4 |
| R2.22h | 50.9 | 95.6 | 368.1 | 1007.8 |
| R3.22h | 93.4 | 273.6 | 544.1 | |
| R4.22h | | | | 360.4 |
| Average | 73.9 | 200.81 | 501.5 | 1838.6 |
| Variation | 21.5 | 93.3 | 176.3 | 1174.9 |
| Average Flux | 3.4 | 9.1 | 22.8 | 83.6 |
| in (ng/cm2/h) | 1.0 | 4.2 | 8.0 | 53.4 |
| skin 1 | 14307.3 | | 3806.2 | 1212.2 |
| skin 2 | 14744.5 | | 3337.5 | 1062.9 |
| skin 3 | 18049.1 | | 5780.4 | 1840.9 |
| skin 4 | | | 4055.4 | |
| Average | 15700.3 | | 4244.89 | 1372.0 |
| Variation | 2045.8 | | 1066.07 | 412.9 |

Typically, 3 or 4 replicates (Table 5: R1, R2, R3, R4) were obtained. Sometimes, however, an experimental problem was evident (e.g., an obvious skin perforation, or a leak from the diffusion cell), in which case only two replicates were possible.

Total recoveries of radioactivity ('mass balance') were less than 100%, primarily because the viscous nature of the donor phases prevented their complete removal from the diffusion cell compartment. The problem increased with increasing HA molecular weight.

Figure 1:
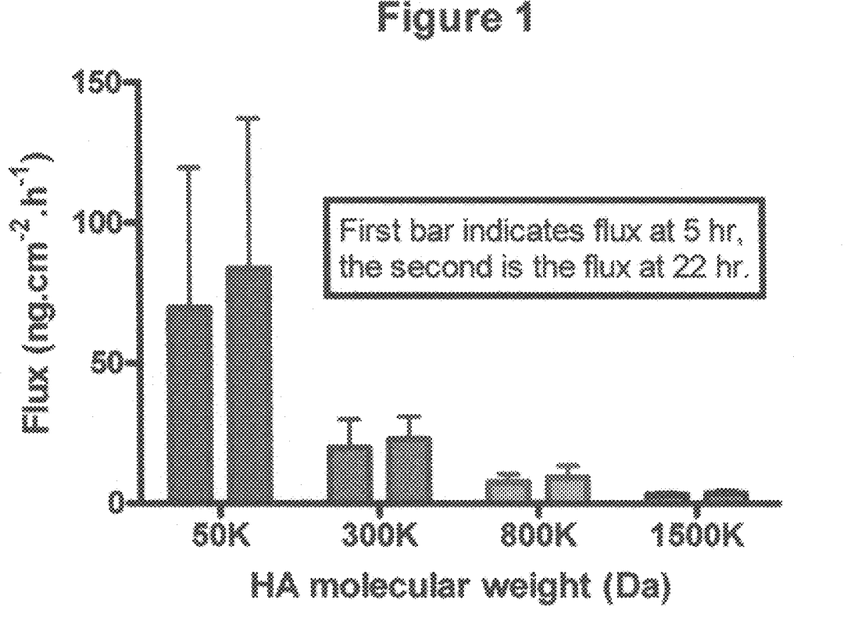
FIG. 1: Skin permeation of four different average molecular weight fractions of radiolabeled hyaluronic acid was investigated as described in example 7. The results are shown in table 5, and visualized in FIG. 1. They indicate that there is an apparent dependence of percutaneous transport (flux) on HA molecular weight, with a better permeation apparent for the lower molecular weight species. There was no significant difference between the apparent fluxes measured at 5 and 22 hours for any of the HA size fractions studied.

These results are visualized in FIG. 1, and they indicate that there is an apparent dependence of percutaneous transport on HA molecular weight, with a better permeation apparent for the lower molecular weight species. There was no significant difference between the apparent fluxes measured at 5 and 22 hours for any of the HA size fractions studied.

Overall, therefore, HA penetration is dependent on HA molecular weight. The lower the molecular weight the better the skin penetration.

However the amount that penetrates the skin corresponds to a small fraction of the applied radioactivity.

Example 8

Topical Distribution of Different Molecular Weight Fractions of HA

Skin uptake and distribution of two different average molecular weight fractions of flourescently labelled hyaluronic acid was investigated using laser scanning confocal microscopy, the average molecular weights of the HA fractions were 300,000 and 50,000 Da.

The fluorescent HA samples were aqueous solutions at a concentration of 1 mg/mL; the fluorescent HA solutions were diluted 10-fold with non-labelled HA of identical molecular weight in distilled water before application.

The skin used for HA application was from the porcine ear. Each HA fraction was applied and tested on at least three separate samples of skin originating from different animals. The skin samples were obtained as fresh and were kept stored frozen for no longer than 2 weeks prior to use.

Prior to the experiment, a thawed skin sample (approx. 0.8 cm$^2$) was sandwiched between donor and receptor phases of simple glass diffusion cells and maintained at 32° C. The donor phase was 0.1 ml of labelled HA solution, and the receptor phase was pH 7.4 buffer.

The fluorescent HA solutions remained in contact with the skin samples for 3 hours, then excess donor solutions were removed, the skin was washed 3 times with pH 7.4 buffer, and dried gently with tissue.

The skin was immediately mounted on a glass slide, stratum corneum side up, and examined microscopically with no further processing using a LSM 410 Invert Laser Scan Microscope (Carl Zeiss, Germany). The system is equipped with an argon-krypton laser having excitation wavelengths of 568 and 488 nm, which were used separately to view the skin and the labelled HA, respectively.

Images were obtained using Plan-neofluar 10x/0.3 and 40x/0.6 objectives, and then subsequently colour-coded digitally so that fluorescence from skin was red, and fluorescence from the labelled HA was green. The images were color-coded and overlaid (or superimposed) using Zeiss LSM confocal software.

In separate experiments, skin samples were examined in the absence of the fluorescent probes. The autofluorescence from porcine skin enabled structural features to be identified. To visualize the distribution of fluorescent HA, confocal images were obtained in the xy-plane (i.e., parallel to skin surface). The skin surface (z=0 μm) was defined as the imaging plane of brightest fluorescence with a morphology characteristic of stratum corneum. Replicate images, using at least three separate pieces of skin, were acquired for each treatment.

Figure 2:
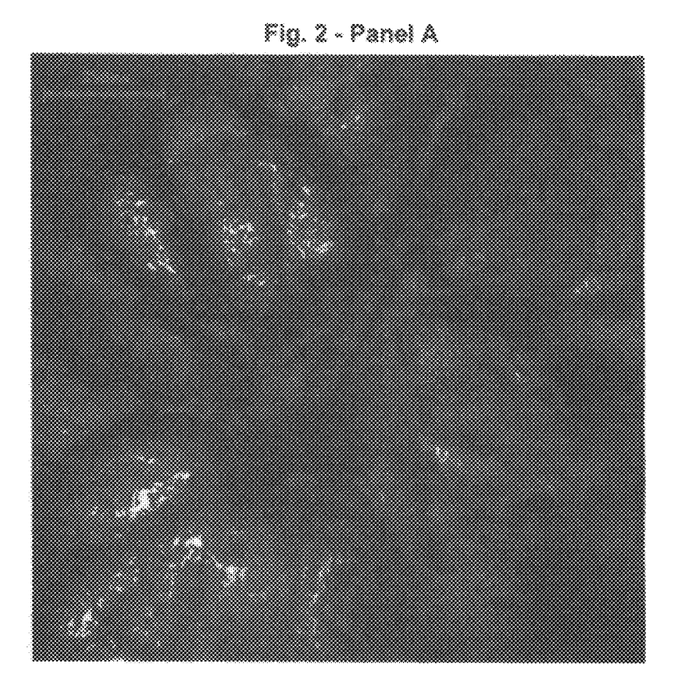
FIG. 2: Skin uptake and distribution of two different average molecular weight fractions of flourescently labelled hyaluronic acid was investigated in example 8, using laser scanning confocal microscopy. The average molecular weights of the HA fractions were 300,000 and 50,000 Da. Flourescently labelled HA of 50,000 Da (F-HA 0.05) was only sparsely and superficially visible on the surface of the stratum corneum, but the labelled HA fraction was clearly visible around and/or in hair follicles.

Flourescently labelled HA of 50,000 Da (F-HA 0.05) was only sparsely and superficially visible on the surface of the stratum corneum, but the labelled HA fraction was clearly visible around and/or in hair follicles. FIG. 2, panel A, shows skin surface (stratum corneum), hair follicle and hair shaft; panel B clearly shows that green fluorescence from HA is primarily visible around and/or in the follicle.

Figure 3:
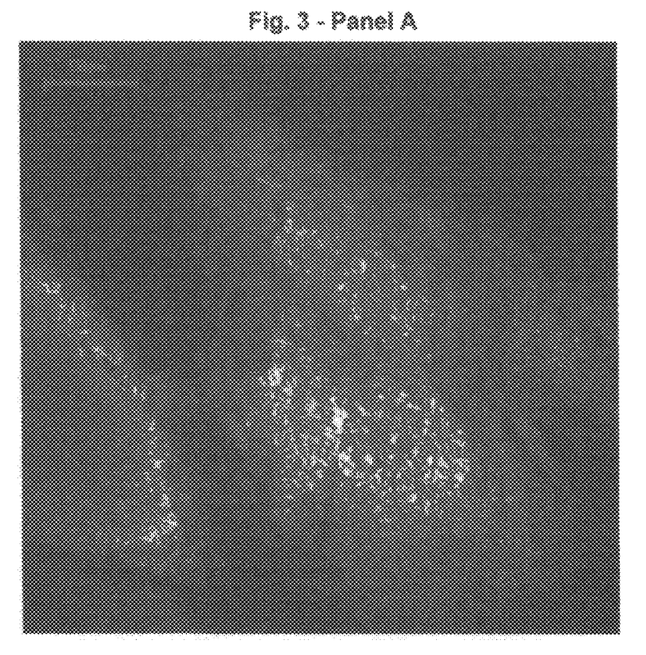
FIG. 3: The sparse fluorescence on the surface of the stratum corneum seen in FIG. 2 was confirmed in another skin sample, which did not have a follicle present.

The sparse fluorescence on the surface of the stratum corneum was confirmed in another skin sample, which did not have a follicle present. FIG. 3, panel A, shows a skin surface; panel B shows that only limited fluorescence from labelled HA is visible on that surface.

Figure 4:
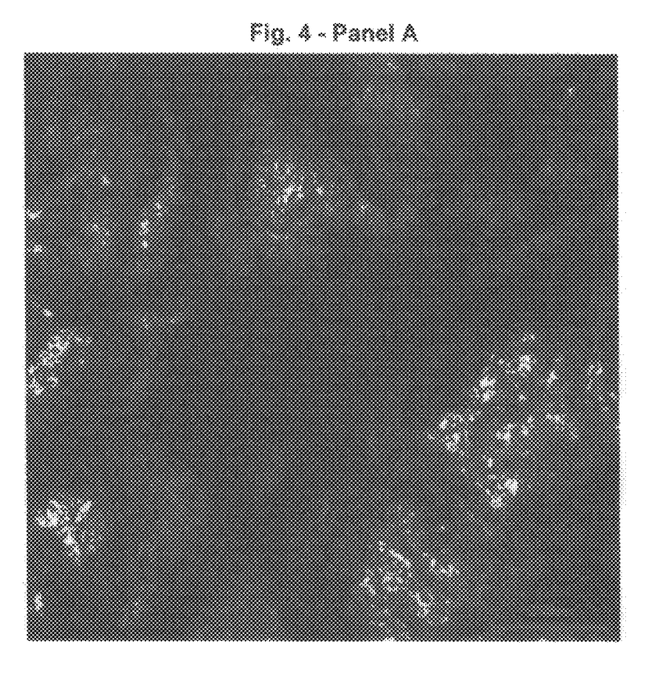
FIG. 4: A similar observation was made with the flourescently labelled HA of 300,000 Da (F-HA 0.30), which also was clearly visible around the hair follicles.

A similar observation was made with the flourescently labelled HA of 300,000 Da (F-HA 0.30), which also was clearly visible around the hair follicles. FIG. 4, panel A, shows a skin surface (stratum corneum), hair follicle and hair shaft; panel B shows the green fluorescence from labelled HA around the follicle.

Figure 5:
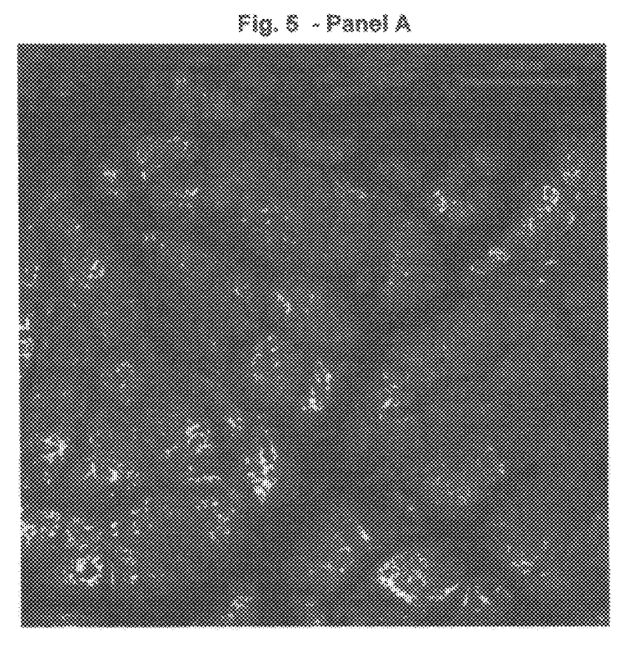
FIG. 5: However, while the labelled HA fraction of 300,000 Da was also only sparsely and superficially visible on the skin surface, it clearly showed a preferential accumulation between the keratinocytes on the skin surface.

However, while the labelled HA fraction of 300,000 Da was also only sparsely and superficially visible on the skin surface, it clearly showed a preferential accumulation between the keratinocytes on the skin surface. FIG. 5, panel A, shows a skin surface; panel B shows that while limited fluorescence from labelled HA is visible on that surface, it is accumulated between the keratinocytes.

Conclusions are, that low molecular weight HA shows some preferential accumulation on, in and around follicular structures in the skin. This could be one possible permeation pathway for low MW HA products of compositions of the invention, that would be of particular interest with respect to the treatment of hair loss or baldness.

There was no evidence for transport across intact stratum corneum of low MW HA of 0.05 MDa as after the removal of HA, only few fluorescent species were found sparsely and superficially on surface layers. Finally, HA of 0.30 MDa shows preferential accumulation between the keratinocytes on the skin surface. This might contribute to improved skin hydration as the HA barrier could restrict the passive transepidermal water loss from the skin.

The invention claimed is:

1. A product comprising a hyaluronic acid or a salt thereof, which product is dried and agglomerated and has:
   (a) a moisture content of less than 5%;
   (b) a particle size, the 50 percentile of which, is between 180 and 1000 microns, as determined by laser diffraction measurement of the particles suspended in isopropanol;
   (c) a dispersibility of less than 30 minutes in an aqueous solvent; and
   (d) a solubility of less than 60 minutes in an aqueous solvent;
wherein the hyaluronic acid is not crosslinked and has a molecular weight up to 1,800,000 Da.

2. The product of claim 1, which has a particle size, the 50 percentile of which, is between 200 and 800 microns.

3. The product of claim 1, wherein the hyaluronic acid or salt thereof has a molecular weight in the range of between 10,000 and 1,500,000 Da.

4. The product of claim 1, wherein the hyaluronic acid or salt thereof has an average molecular weight in the range of between 10,000 and 800,000 Da.

5. The product of claim 1, which comprises an inorganic salt of hyaluronic acid.

6. The product of claim 1, wherein the hyaluronic acid or salt thereof has an average molecular weight in the range of 20,000 and 600,000.

7. The product of claim 1, which has a moisture content of less than 2%.

8. The product of claim 1, which has a dispersibility of less than 10 minutes in an aqueous solvent.

9. The product of claim 1, which has a dispersibility of less than 5 minutes in an aqueous solvent.

10. The product of claim 1, which has a solubility of less than 30 minutes in an aqueous solvent.

11. The product of claim 1, which has a solubility of less than 15 minutes in an aqueous solvent.

12. The product of claim 1, which has a solubility of less than 10 minutes in an aqueous solvent.

13. The product of claim 1, which has a solubility of less than 5 minutes in an aqueous solvent.

14. A pharmaceutical composition comprising a product of claim 1 and a pharmaceutically acceptable carrier, excipient or diluent.

15. A pharmaceutical composition comprising a product of claim 1 as a vehicle, and a pharmacologically active agent.

16. A medicament capsule or microcapsule comprising a product of claim 1.

17. A method of producing a product of claim 1, comprising the steps of:
   a) drying a product comprising hyaluronic acid or a salt thereof; and
   b) agglomerating the dried product.

18. The method of claim 17, wherein the drying step is done using a spray-dryer or a Rotary Atomizer.

19. The method of claim 17, wherein the drying step is done using a Two-Fluid-Nozzle (TFN) spray-dryer.

20. The method of claim 19, wherein the spray-drying was done using a TFN spray-dryer and the following condition ranges:
   Inlet temperature: 100-200° C.,
   Outlet temperature: 40-90° C.,
   Nozzle atomization pressure: 2-10 bar,
   Nozzle air temperature: 40-100° C., and
   Feed temperature: 40-100° C.

21. The method of claim 17, wherein the agglomerating step is done using a fluidized bed.

22. The method of claim 21, wherein the fluidized bed inlet temperature is in the range of 30-80° C., and wherein the aqueous solution of the powder is sprayed on the dried powder at a rate corresponding to an outlet temperature of 25-50° C.

23. The method of claim 17, wherein the agglomerating step is done using a water-solvent mixture having a water:solvent ratio of between 0:100 and 50:50.

24. The method of claim 23, wherein the solvent is an alcohol.

25. The method of claim 24, wherein the solvent is isopropanol.

26. The method of claim 17, wherein the drying and agglomerating is done in one step using a fluidized spray-dryer.

* * * * *

UNITED STATES PATENT AND TRADEMARK OFFICE
CERTIFICATE OF CORRECTION

| | | |
|---|---|---|
| PATENT NO. | : 7,956,180 B2 | |
| APPLICATION NO. | : 11/132829 | |
| DATED | : June 7, 2011 | |
| INVENTOR(S) | : Bach et al. | |

It is certified that error appears in the above-identified patent and that said Letters Patent is hereby corrected as shown below:

Title page, Item (73), Assignee: please correct the name of the assignee as follows:

Delete "Novozymes A/S" and insert --Novozymes Biopolymer A/S--.

Signed and Sealed this
Eleventh Day of October, 2011

David J. Kappos
*Director of the United States Patent and Trademark Office*